United States Patent
Wagner et al.

[11] Patent Number: 5,271,747
[45] Date of Patent: Dec. 21, 1993

[54] MENISCUS PLATFORM FOR AN ARTIFICIAL KNEE JOINT

[75] Inventors: Heinz Wagner, Schwarzenbruck, Fed. Rep. of Germany; Roland Willi, Neftenbach, Switzerland

[73] Assignees: Sulzer Medizinaltechnik AG, Winterthur; Protek AG, Muensingen-Bern, both of Switzerland

[21] Appl. No.: 993,220

[22] Filed: Dec. 18, 1992

[30] Foreign Application Priority Data

Jan. 14, 1992 [CH] Switzerland ............. 00090/92

[51] Int. Cl.⁵ .................................. A61F 2/38
[52] U.S. Cl. .................................... 623/20
[58] Field of Search ......................... 623/18, 20

[56] References Cited

U.S. PATENT DOCUMENTS 5,116,376  5/1992  May ........................... 623/20

FOREIGN PATENT DOCUMENTS

| 0186471 | 7/1986 | European Pat. Off. | 623/20 |
| 2636816 | 2/1977 | Fed. Rep. of Germany | |
| 3528204 | 2/1986 | Fed. Rep. of Germany | 623/20 |
| 2663536 | 12/1991 | France | 623/20 |
| 2008424 | 5/1992 | World Int. Prop. O. | 623/20 |

Primary Examiner—David Isabella
Attorney, Agent, or Firm—Townsend and Townsend Khourie and Crew

[57] ABSTRACT

With the invention is shown a meniscus platform for an artificial knee joint, which consists of a metal platform (1) and a metal slide member (3) sliding thereon at right angles to the tibia axis (17), which on its upper side comprises sliding surfaces (4, 5) and a guide bead (8) for the condyles (13, 14) of a femur part (11). The sliding movement between the metal slide member (3) and the metal platform (1) is restricted by a guiding pin (10) in the metal platform, which engages in an oblong hole (9) in a slide member (3) made of metal. The metal slide member (3) can rotate around the guiding pin (10) and can be displaced along its oblong hole (9). The rotational movement of the slide member (3) is restricted by a limiting recess (15), which encloses a part of the eminentia (19) in the region of the rear cruciate ligament.

6 Claims, 2 Drawing Sheets

1

MENISCUS PLATFORM FOR AN ARTIFICIAL KNEE JOINT

BACKGROUND OF THE INVENTION

The invention relates to a meniscus platform for an artificial knee joint having a metal platform, which on its under side is connected via attachment members to the tibia comprises. It includes a recess for the rear cruciate ligament and untouched parts of the eminentia and supports a sliding member which, on its upper side, has sliding surfaces and a guide bead for the condyles of a femur part.

The problems of and solutions for artificial knee joints are described in detail in U.S. Pat. No. 4,309,778. The solutions shown try to imitate the movement mechanism of the natural knee joint and to make its design as safe as possible with respect to the guidance of the movable components. They require a correspondingly great amount of space for safeguarding the guiding movement, around which a resection in the osseous tissue of the tibia bone has to be performed.

SUMMARY OF THE INVENTION

The object of present invention is to keep the amount of bone material at the tibia to be removed as small as possible without departing too much from the path of movement of the natural knee joint. The invention has the advantage that because of the small resection part the rear cruciate ligament and also the collateral ligaments may be retained and assist in restricting the movement of movable components similar to the natural knee. Thus, fewer mechanical stops are required to guide the movable components.

DESCRIPTION OF THE PREFERRED EMBODIMENTS

Figure 1:
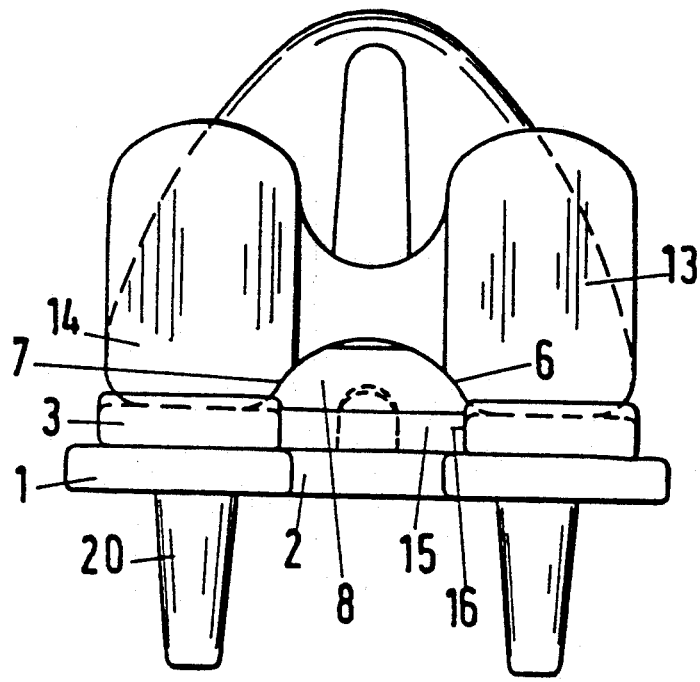
FIG. 1 is a view from the rear of a knee joint prosthesis with a tibia platform, slide member and femur part constructed in accordance with the present invention.

In the figures there is shown a meniscus platform for an artificial knee joint, which includes a metal platform 1 and a metal slide member 3 sliding thereon at right angles to the tibial axis 17, which on its upper side has sliding surfaces 4, 5 and a guide bead 8 for the condyles 13, 14 of a femur part 11. The sliding movement between metal slide member 3 and metal platform 1 is restricted by a guiding pin 10 in the metal platform, which engages in an oblong hole 9 in a slide member 3 made of metal. The metal slide member 3 can rotate around the guiding pin 10 and may be displaced along its oblong hole 9. The rotational movement of the slide member 3 is restricted by a limiting recess 15, which encloses a part of the eminentia 19 in the region of the rear cruciate ligament.

Figure 3:
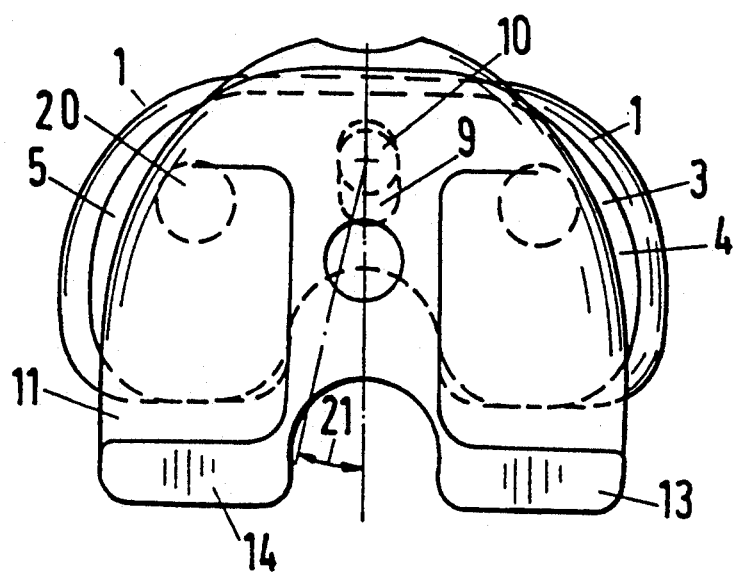
FIG. 3 is a lateral view of a section through the prosthesis shown in FIG. 1 and shows the tibia.
Figure 2:
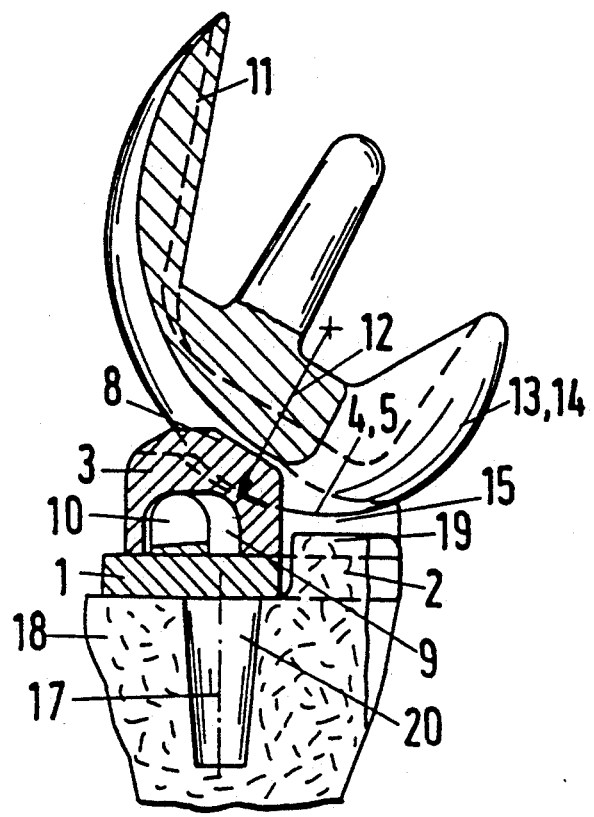
FIG. 2 is a plan view of the prosthesis shown in FIG. 1.

The metal platform 1 is attached with two attachment members 20 in the form of pegs in the tibia 18 and has a recess 2, into which the untouched part of the eminentia 19 in the region of the rear cruciate ligament protrudes. In a plane at right angles to the tibia axis 17 slides the slide member 3, which, as can be seen in FIG. 3, has smaller lateral dimensions for the metal inside dimension than recess 2, so that it is possible to swivel slide member 3 from the central position with the femur part 11 guided thereon by an angle 21, without the slide member 3 protruding over the metal platform 1. An angle 21 of between 5° and 20° is specified as the maximum swivel angle. For this reason the lateral cheeks 16 of the limiting recess 14 are set back. The condyles 13, 14 and the sliding surfaces 4, 5 slide on common cylindrical surfaces having a radius 12. The guide bead 8 lies between the two condyles 13, 14 and guides them on the inside with lateral guides 6, 7, which have the same axis of rotation as the cylindrical surfaces of the condyles 13, 14. The oblong hole 9 lies in the sagittal direction when the slide member is not swivelled and has a guide length of up to 8 mm for the guiding pin 10 in the sagittal direction.

What is claimed is:

1. A tibial implant for a knee joint comprising: a metal platform adapted to be implanted in a tibia of a patient, the platform including a recess shaped and positioned to accommodate a rear cruciate ligament and a portion of an eminentia of the patient, the platform having a support surface which is substantially perpendicular to an axis of the tibia; a metallic sliding member carried on the support surface of the platform including sliding surfaces for cooperating with femoral condyle slide surfaces and having a substantially cylindrical shape with a constant radius of curvature, the slide member including a cutout aligned with the recess when the slide member and the platform are in rotational alignment with each other, the cutout being shaped to accommodate a portion of the patient's eminentia with clearance between lateral sides of the sliding member defining the cutout and the eminentia; and means slidably movably connected the slide member to the platform and permitting limited linear sliding motions between them in anterior and posterior directions and unlimited relative rotational movement between them about an axis substantially parallel to the axis of the tibia; whereby, upon implantation of the platform and the slide member, relative rotational movement between the platform and the slide member are limited by contact between the portion of the patient's eminentia extending into the cutout and the later sides of the cutout.

2. A tibial implant according to claim 1 wherein a distance between the lateral sides of the cutout is greater than a spacing between lateral walls of the platform defining the recess.

3. An implant according to claim 1 wherein the connecting means comprises a pin projecting perpendicularly from the support surface of the platform and an elongated slot in the slide member adapted to be placed over the pin when the slide member is carried by the support surface of the platform, the slot limiting linear movements between the slide member and the support surface and the pin defining an axis of rotation for the rotational movement of the slide member relative to the platform.

4. An implant according to claim 1 wherein the connecting means and the cutout are dimensioned and arranged to limit relative rotational movements between the platform and the slide member to between 5° and 20°.

5. A prosthetic knee joint comprising:
a femoral implant adapted to be implanted in a femur of a patient and defining spaced-apart condyles having cylindrically shaped condyle surfaces;

a platform for implantation in a tibia of the patient, the platform defining a planar support surface substantially perpendicular to an axis of the tibia, an anterior recess in the platform shaped to accommodate a rear cruciate ligament and an eminentia of the patient when implanted, and an upright member projecting perpendicularly from the support surface; and a slide member carried on the support surface of the platform and including an elongated slot engaging the projecting member so that the slide member can linearly slide relative to the platform within limits defined by the interengaging upright member and the slot and can freely rotationally slide about the upright member, the slide member including a cutout overlying the recess in the platform and bounded by lateral sides spaced from each other sufficiently so that, upon implantation of the platform and the slide member, a spacing between the sides is greater than a corresponding transverse width of a portion of the eminentia disposed in the cutout;

whereby, upon implantation of the prosthetic knee, relative rotational movements between the platform and the slide member are limited by an engagement of the lateral sides of the cutout by the portion of the patient's eminentia in the cutout.

6. A prosthetic knee joint comprising:

a femoral implant constructed of metal, adapted to be implanted in a femur of a patient and defining spaced-apart condyles having cylindrically shaped condyle surfaces with a constant radius of curvature;

a platform constructed of metal for implantation in a tibia of the patient, the platform defining a planar support surface substantially perpendicular to an axis of the tibia, a rearwardly open anterior recess in the platform shaped to accommodate a rear cruciate ligament and an eminentia of the patient when implanted, and an upright member projecting perpendicularly from the support surface; and a slide member constructed of metal carried on the support surface of the platform and including an elongated slot extending in an anterior-posterior direction engaging the projecting member so that the slide member can linearly slide relative to the platform in the anterior-posterior directions within limits defined by the interengaging upright member and the slot and can freely rotate about the upright member, the slide member including a rearwardly open cutout overlying the recess in the platform and bounded by lateral sides spaced from each other sufficiently so that, upon implantation of the platform and the slide member, a spacing between the sides is greater than a corresponding transverse width of a portion of the eminentia disposed in the cutout, the slide member further including slide surfaces on a side of the slide member facing away from the platform, the slide surfaces being cylindrically shaped to cooperate with the condyle surfaces and permit relative slidable motions between the condyle surfaces and the slide surfaces, the cylindrical slide surfaces having a constant radius of curvature;

whereby, upon implantation of the prosthetic knee, relative rotational movements between the platform and the slide member are limited by an engagement of the lateral sides of the cutout by the portion of the patient's eminentia in the cutout; and whereby, upon implantation of the prosthetic knee, bodily fluid accumulates between the condyle surfaces and the slide surfaces and forms a lubricating film preventing metal-to-metal contact between the condyle surfaces and the slide surfaces.

* * * * *